(12) United States Patent
Lin et al.

(10) Patent No.: US 8,828,705 B1
(45) Date of Patent: Sep. 9, 2014

(54) MAGNETIC MESOPOROUS MATERIAL FOR THE SEQUESTRATION OF ALGAE

(75) Inventors: Victor Shang-Yi Lin, Ames, IA (US); Show-Ling Lee, legal representative, Ames, IA (US); Brian G. Trewyn, Ames, IA (US); Kapil Kandel, Ames, IA (US); Igor Ivan Slowing, Ames, IA (US)

(73) Assignee: Iowa State University Research Foundation, Inc., Ames, IA (US)

(*) Notice: Subject to any disclaimer, the term of this patent is extended or adjusted under 35 U.S.C. 154(b) by 79 days.

(21) Appl. No.: 13/300,343

(22) Filed: Nov. 18, 2011

Related U.S. Application Data

(60) Provisional application No. 61/415,076, filed on Nov. 18, 2010.

(51) Int. Cl.
C12N 11/00 (2006.01)

(52) U.S. Cl.
USPC .......................................... 435/243; 423/335

(58) Field of Classification Search
CPC ................................. C12N 11/01; C12N 1/12
USPC .......................................... 435/243; 423/335
See application file for complete search history.

(56) References Cited

U.S. PATENT DOCUMENTS

| | | | |
|---|---|---|---|
| 4,279,756 A * | 7/1981 | Weiss et al. ................... | 210/667 |
| 4,554,390 A | 11/1985 | Curtain et al. | |
| 7,625,490 B2 | 12/2009 | Cort | |
| 8,361,623 B2 | 1/2013 | Lin et al. | |
| 2006/0018966 A1 | 1/2006 | Lin et al. | |
| 2006/0154069 A1 | 7/2006 | Lin et al. | |
| 2008/0021232 A1 | 1/2008 | Lin et al. | |
| 2008/0175783 A1 | 7/2008 | Park et al. | |
| 2010/0196971 A1 | 8/2010 | Lin et al. | |

FOREIGN PATENT DOCUMENTS

| | | |
|---|---|---|
| JP | 2006069824 A | 3/2006 |
| WO | WO-0132308 A1 | 5/2001 |
| WO | WO-2004054708 A2 | 7/2004 |
| WO | WO-2008060571 A2 | 5/2008 |
| WO | WO-2009017425 A1 | 2/2009 |
| WO | WO-2010088001 A2 | 8/2010 |
| WO | WO-2010088001 A3 | 12/2010 |

OTHER PUBLICATIONS

Zheng et al., Advanced Materials, vol. 20, No. 4, p. 805-809, 2008.*
Doadrio et al., Journal of Material Chemistry, vol. 16, p. 462-466, 2006.*
Bargiel, Jeffrey T., "Commercialization of Lateral Displacement Array for Dewatering of Microalgae", Submitted in partial fulfillment of the requirements for the degree of Master of Science Thesis Committee: Robert Brown, Ph.D. J. Kevin Berner, Ph.D. Edward Caner Cyrus Taylor, Ph.D. Christopher Lane, Ph.D. Department of Physics Case Western Reserve Univer, (May 2009), 53 pgs.
Chan, W. C, et al., "Quantum dot bioconjugates for ultrasensitive nonisotopic detection", Science, 281(5385), (Sep. 25, 1998), 2016-8.
Chen, Y. M., et al., "Flotation removal of algae from water", Colloids and Surfaces B: Biointerfaces, 12(1), (Oct. 15, 1998), 49-55.
Divakaran, Ravi, et al., "Flocculation of algae using chitosan", Journal of Applied Phycology, 14(5), (2002), 419-422.
Doyle, P. S, et al., "Self-assembled magnetic matrices for DNA separation chips.", Science, 295(5563), (Mar. 22, 2002), 2237.
Giri, Supratim, et al., "Stimuli-Responsive Controlled-Release Delivery System Based on Mesoporous Silica Nadorods Capped with Magnetic Nanoparticles", Angew. Chem. Int. Ed. 2005, 44, (2005), 5038-5044.
Gu, H., et al., "Using Biofunctional Magnetic Nanoparticles to Capture Vancomycin-Resistant Enterococci and Other Gram-Positive Bacteria at Ultralow Concentration", J. Am. Chem. Soc., 125(51), (2003), 15702-15703.
Hung, Yung-Tse, et al., "Algae Harvest Energy Conversion", Handbook of Environmental Engineering, vol. 11: Environmental Bioengineering, (2010), 723-741.
Linton, Peter, et al., "Growth and Morphology of Mesophorous SBA-15 Particles", Chem. Mater. 2008, 20, (Apr. 10, 2008), pp. 2878-2880.
Middlebrooks, E. Joe, et al., "Techniques for Algae Removal from Wastewater Stabilization Ponds", Journal (Water Pollution Control Federation), 46(12), (Dec. 1974), 2676-2695.
Uduman, Nyomi, et al., "Dewatering of microalgal cultures: A major bottleneck to algae-based fuels", Journal of Renewable and Sustainable Energy, 2, (2010), 012701-15.
Wang, J., et al., "Superparamagnetic Fe2O3 Beads—CdSe/ZnS Quantum Dots Core-Shell Nanocomposite Particles for Cell Separation", Nano Lett., 4(3), (2004), 409-413.
Xu, C., et al., "Dopamine as A Robust Anchor to Immobilize Functional Molecules on the Iron Oxide Shell of Magnetic Nanoparticles", J. Am. Chem. Soc., 126(32), (2004), 9938-9939.
Yiu, H H P, et al., "Synthesis of novel magnetic iron metal-silica (Fe-SBA-15) and magnetite-silica (Fe3O4-SBA-15) nanocomposites with a high iron content using temperature-programed reduction", Nanotechnology 19, (2008), 7 pgs.
Zhang, Xuezhi, et al., "Harvesting algal biomass for biofuels using ultrafiltration membranes.", Bioresour Technol., 101(14), (Jul. 2010), 5297-304.
"U.S. Appl. No. 12/698,656, Notice of Allowance mailed Sep. 18, 2012", 10 pgs.
"U.S. Appl. No. 12/698,656, Preliminary Amendment mailed Apr. 13, 2010", 6 pgs.
"U.S. Appl. No. 12/698,656, Response filed Aug. 22, 2012 to Restriction Requirement mailed May 31, 2012", 7 pgs.
"U.S. Appl. No. 12/698,656, Restriction Requirement mailed May 31, 2012", 11 pgs.

(Continued)

Primary Examiner — Susan Hanley
Assistant Examiner — Damon B Bowe
(74) Attorney, Agent, or Firm — Schwegman Lundberg & Woessner, P.A.

(57) ABSTRACT

The present invention provides a magnetic mesoporous nanoparticle that includes a mesoporous silicate nanoparticle and iron oxide. The present invention also provides a method of using magnetic mesoporous nanoparticles to sequester microorganisms from a media.

19 Claims, 6 Drawing Sheets
(2 of 6 Drawing Sheet(s) Filed in Color)

(56) References Cited

OTHER PUBLICATIONS

"International Application U.S. Appl. No. PCT/US2010/000289, International Preliminary Report on Patentability mailed Aug. 11, 2011", 20 pgs.

"International Application U.S. Appl. No. PCT/US2010/000289, Invitation to Pay Additional Fee mailed Jun. 21, 2010", 13 pgs.

"International Application U.S. Appl. No. PCT/US2010/000289, Search Report mailed Sep. 14, 2010", 12 pgs.

"International Application U.S. Appl. No. PCT/US2010/000289, Search Report mailed Oct. 22, 2010", 12 pgs.

"International Application U.S. Appl. No. PCT/US2010/000289, Written Opinion mailed Sep. 14, 2010", 18 pgs.

"International Application U.S. Appl. No. PCT/US2010/000289, Written Opinion mailed Oct. 22, 2010", 18 pgs.

Capasso, J. M., et al., "A colorimetric assay for determination of cell viability in algal cultures", Biomolecular Engineering, 20(Issues 4-6), (2003), 4-6.

Cazin, C. S. J., et al., "Versatile Methods for the Synthesis of Si(OR)sub 3-Functionalised Imidazolium Salts, Potential Precursors for Heterogeneous NHC Catalysts and Composite Materials", Synthesis 2005, No. 4, (2005), 622-626.

Cha, S., et al., "Colloidal Graphite-Assisted Laser Desorption/Ionization Mass Spectrometry and MSn of Small Molecules. 1. Imaging of Cerebrosides Directly from Rat Brain Tissue", Analytical Chemistry, 79(6), (2007), 2373-2385.

Chisti, Y., "Biodiesel from microalgae", Biotechnology Advances, 25, (2007), 294-306.

Dayananda, C., et al., "Autotrophic cultivation of *Botryococcus braunii* for the production of hydrocarbons and exopolysaccharides in various media", Biomass & Bioenergy, 31, (2007), 87-93.

Gadenne, B., et al., "Supported ionic liquids ordered mesoporous silicas containing covalently linked ionic species", Chemical Communications, 15, (2004), 1768-1769.

Hall, S. R., et al., "Template-directed synthesis of bi-functionalized organo-MCM-41 and phenyl-MCM-48 silica mesophases", Chem. Commun., (1999), 201-202.

Herrero, M. A., et al., "Recent Advances in the Covalent Functionalization of Carbon Nanotubes", Mol. Cryst. Liq. Cryst., 483, (2008), 21-32.

Hirsch, A., et al., "Functionalization of Carbon Nanotubes", Topics in Current Chemistry—Functional Molecular Nanostructures, vol. 245, (2005), 193-237.

Kim, T.-W., et al., "Structurally Ordered Mesoporous Carbon Nanoparticles as Transmembrane Delivery Vehicle in Human Cancer Cells", Nano Letters, 8(11), (2008), 3724-3727.

Leon-Banares, R., et al., "Transgenic microalgae as green cell-factories", TRENDS in Biotechnology, 22(1), (2004), 45-52.

MacQuarrie, D. J, "Organically modified hexagonal mesoporous silicas—Clean of high loading and non-catalytic second groups on catalytic activity of amine-derivatised materials", Green Chemistry, vol. 1, No. 4, DDOI: 10.1039/a904692e, (Sep. 6, 1999), 195-198.

Nepal, D., et al., "Chapter 4—Functionalization of Carbon Nanotubes", Functional Nanomaterials, Geckeler, K. E., et al., Editors, American Scientific Publishers, (2006), 57-79.

Pan, C., et al., "Carbon Nanotubes as Adsorbent of Solid-Phase Extraction and Matrix for Laser Desorption/Ionization Mass Spectrometry", J. Am. Soc. Mass Spectrom., 16, (2005), 263-270.

Pan, C., et al., "Using Oxidized Carbon Nanotubes as Matrix for Analysis of Small Molecules by MALDI-TOF MS", J. Am. Soc. Mass Spectrom., 16, (2005), 883-892.

Soeng, H., "Controlling the Selectivity of Competitive Nitroaldol Condensation by Using Bifunctionalized Mesoporous silica Nanosphere-Based Catalytic System", Journal of the American Chemical Society, vol. 126, No. 4, (Sep. 1, 2004), 1010-1011.

Udayakumar, S., et al., Imidazolium derivatives functionalized MCM-41 for catalytic conversion of carbon dioxide to cyclic carbonate—, Catalysis Communications, 10(5), (2009), 659-664.

Van Meter, D. S., et al., "Characterization of surface—confined ionic liquid stationary phases: impact of cation and anion identity on retention", Analytical and Bioannalytical Chemistry 393(1), (2008), 283-294.

Zhang, H., et al., "Colloidal Graphite-Assisted Laser Desorption/Ionization MS and MSn of Small Molecules. 2. Direct Profiling and MS Imaging of Small Metabolites from Fruits", Analytical Chemistry, 79(17), (2007), 6575-6584.

Zhila, N. O., et al., "Effect of Nitrogen Limitation on the Growth and Lipid Composition of the Green Alga *Botryococcus braunii* Kutz IPPAS H-252", Russian Journal of Plant Physiology, vol. 52(3), (2005), 311-319.

\* cited by examiner

MAGNETIC MESOPOROUS MATERIAL FOR THE SEQUESTRATION OF ALGAE

CROSS-REFERENCE TO RELATED APPLICATIONS

This application claims the benefit of priority of U.S. Provisional Application No. 61/415,076, filed Nov. 18, 2010, the disclosure of which is incorporated herein by reference in its entirety.

STATEMENT OF GOVERNMENT SUPPORT

This invention was made with government support under Grant No. DE-AC02-07CH11358 and Grant No. DE-FG26-0NT08854 awarded by the Department of Energy. The government has certain rights in the invention.

BACKGROUND OF THE INVENTION

The need for energy is a major issue throughout the world today. As compared to petroleum sources, fuels derived from biological organisms (biofuels) can be potentially obtained in a more environmentally sustainable fashion. For example, the use of algae as a source of biofuel production has gained enormous research interest. Algae can use photosynthesis to convert carbon dioxide to lipids and hydrocarbons, useful as biofuel with or without further processing beyond the initial extraction. Algae are also valuable as a food source, as well as a source of other valuable materials, including vitamins, color pigment, essential fatty acids, amino acids, pharmaceutically active substances, and other chemicals. Algae can be cultivated in aqueous conditions of both freshwater and seawater. Algae can grow very quickly, and have been known to double their biomass in 24 hours. Algae can be grown year-round with much less land-demand than conventional agriculture.

An important step in the derivation of fuel or other products from algae, as well as in water-purification processes, is the sequestration of algae from a liquid medium. Methods of separating algae from water include, for example, coagulation, flocculation, flotation, centrifugation, filtration, and gravity sedimentation. However, these methods often suffer from expensive inefficiencies due to the nature of the separation. For example, methods of sequestering algae from water using filtration generally have the disadvantage that algae tends to block the filter over time, requiring large amounts of pressure and energy to force the media through both the filter and the accumulating algae. Additionally, cleaning microorganisms from a filter can be time consuming and difficult, and the process of recovering the microorganisms from the filter can be fatal to the microorganisms. Algae has a density very close to that of water, and is small with a typical cell size of from 3-30 µm in diameter. The volume of water from which algae is to be separated can be very high.

The separation of algae from water can be time and energy intensive, and can serve as an economic bottleneck to the use of algae as a biofuel source and to the efficient purification of drinking water.

SUMMARY

In various embodiments, the present invention provides a magnetic mesoporous nanoparticle. The nanoparticle includes a mesoporous silicate nanoparticle. The nanoparticle also includes iron oxide. The magnetic mesoporous nanoparticle is magnetic. The magnetic mesoporous nanoparticle has a mesoporous structure.

In some embodiments, the magnetic mesoporous nanoparticle includes an adsorbed microorganism, wherein the microorganism is adsorbed to the pores or surface of the magnetic mesoporous nanoparticle. The microorganism can be an algae. In some embodiments, the magnetic mesoporous nanoparticle can include one or more amino($C_1$-$C_{20}$)alkyl groups with alkyl units covalently bound to the magnetic mesoporous nanoparticle, wherein the $C_1$-$C_{20}$ alkyl groups are optionally interrupted by one or two —NH— groups. In some embodiments, the iron oxide can be $Fe_3O_4$.

In various embodiments, the present invention also provides a method of using magnetic mesoporous nanoparticles to sequester a microorganism from a media. The method includes contacting a mixture including one or more microorganisms and a media with a plurality of magnetic mesoporous nanoparticles. The contacting is sufficient to adsorb the microorganisms to the pores or surface of the magnetic mesoporous nanoparticles. The method also includes exposing the magnetic mesoporous nanoparticles to a magnetic field. The exposure to the magnetic field is sufficient to concentrate the adsorbed microorganism.

In some embodiments, the media can be water. The microorganism can be algae. In some embodiments, the method further provides separating the magnetic mesoporous nanoparticles with an adsorbed microorganism from the media. The method can further provide desorbing the adsorbed microorganism from the magnetic mesoporous nanoparticles with an adsorbed microorganism. The method can also further provide separating the desorbed microorganism from the magnetic mesoporous nanoparticles.

In various embodiments, the present invention provides a method of making meganetic mesoporous nanoparticles. The method includes condensing an alkoxysilane, to give a mesoporous silicate nanoparticle. The method also includes contacting the mesoporous silicate nanoparticle with an iron precursor, to give a magnetic mesoporous nanoparticle.

In various embodiments, the present invention provides a method of using magnetic mesoporous nanoparticles to sequester algae from water. The method includes contacting a mixture including one or more algae and water with one or more magnetic mesoporous nanoparticles. The magnetic mesoporous nanoparticle includes a mesoporous silicate nanoparticle and $Fe_3O_4$. The contacting is sufficient to adsorb the algae to the pores or surface of the magnetic mesoporous nanoparticles. The method further includes exposing the magnetic mesoporous nanoparticle with the adsorbed algae to a magnetic field. The exposure to the magnetic field is sufficient to concentrate the adsorbed microorganisms. In some embodiments, the method further provides separating the magnetic mesoporous nanoparticles with the adsorbed algae from the water. The method can further provide separating the desorbed algae from the magnetic mesoporous nanoparticles. The method can further provide reusing the magnetic mesoporous nanoparticles for another adsorption cycle.

The present invention provides benefits and advantages over other methods of sequestering a microorganism from a media. The present invention can be more efficient than other methods of sequestering microorganisms, including for example by taking less time than other methods, by requiring less energy than other methods, by using cheaper starting materials than other methods, or by allowing the reuse of materials in a more facile and practical way than with other methods. The present invention can avoid the addition of soluble chemicals to the media, which some methods require to facilitate the sequestration. The addition of soluble chemicals can sometimes prevent the facile reuse or consumption of the media, and can kill the microorganism. The present invention can avoid the high-energy demands of filtration methods, which can require high pressures and tend to result in clogging of the filter necessitating a backwash or filter-cleaning procedure. The present invention can have less moving parts than other methods of microorganism sequestration. In some embodiments, the nanoparticles of the present invention can advantageously be reused through multiple sequestration cycles.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention, however, one skilled in the art will understand that portions of the example or aspect may be used in combination with other examples or aspects of the invention.

The patent or application file contains at least one drawing executed in color. Copies of this patent or patent application publication with color drawing(s) will be provided by the Office upon request and payment of the necessary fee.

Figure 1:
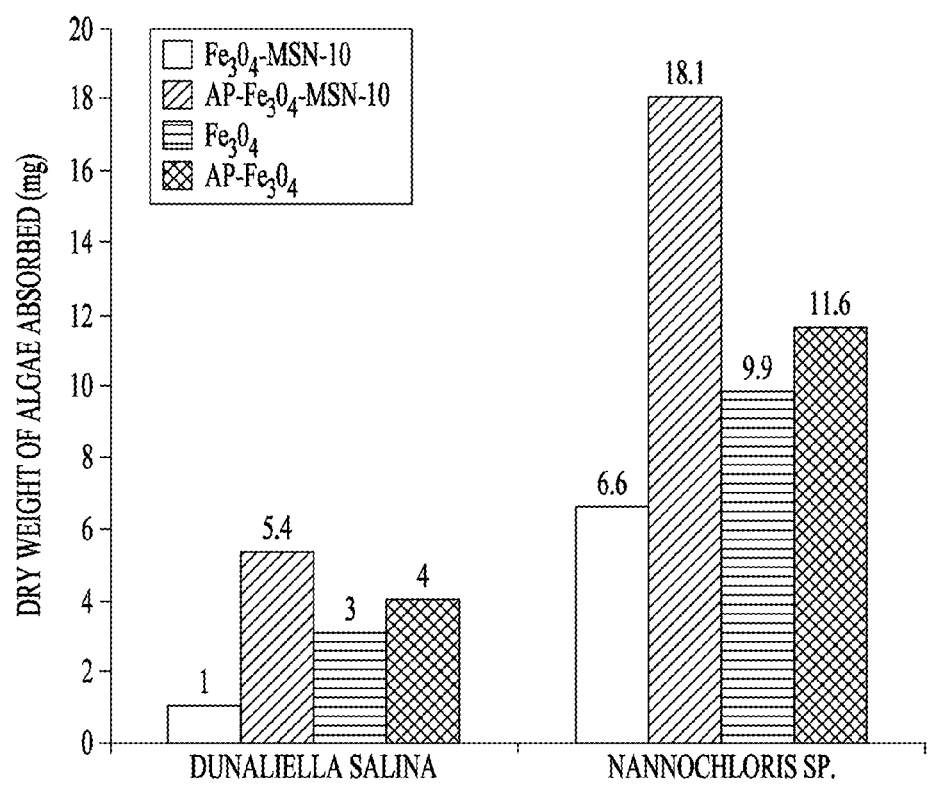

FIG. 1 is a graph of the dry weight of algae adsorbed on various nanoparticles.

Figure 2A:
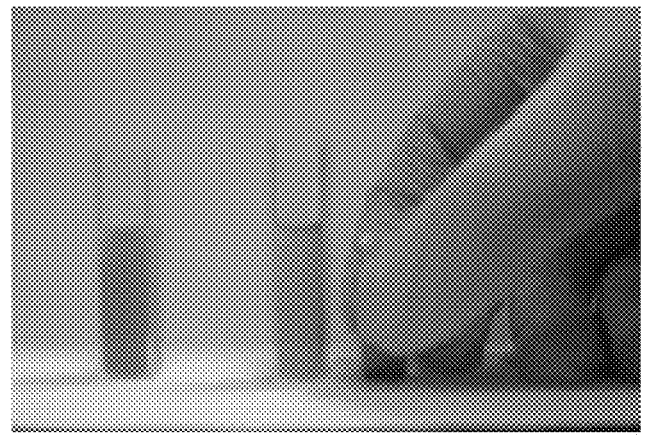

FIG. 2A is a movie still after the adsorption of *Dunaliella salina* by AP-$Fe_3O_4$-MSN-10 nanoparticles.

Figure 2B:
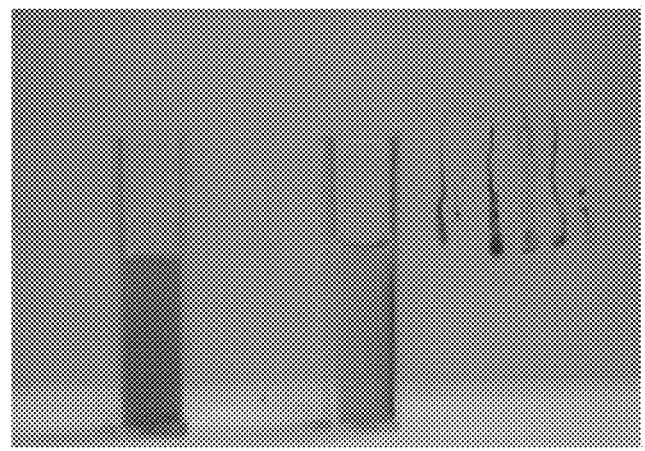

FIG. 2B is a movie still after the adsorption of *Dunaliella salina* by AP-$Fe_3O_4$-MSN-10 nanoparticles.

Figure 2C:
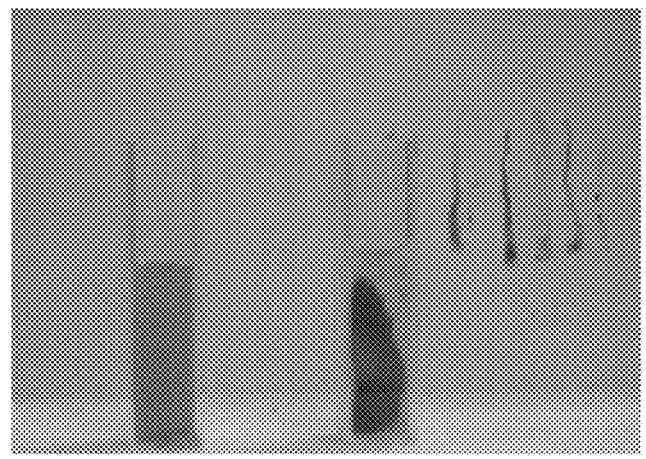

FIG. 2C is a movie still after the adsorption of *Dunaliella salina* by AP-$Fe_3O_4$-MSN-10 nanoparticles.

Figure 3A:
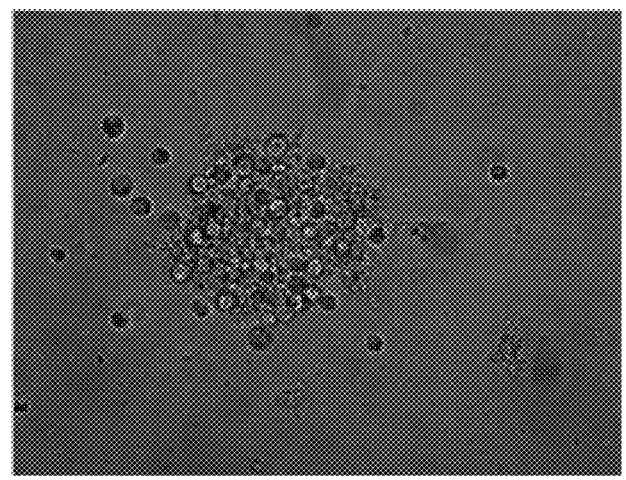

FIG. 3A is a microscope image of AP-$Fe_3O_4$-MSN-10 nanoparticles after adsorption of *Dunaliella salina*.

Figure 3B:

FIG. 3B is a microscope image of AP-$Fe_3O_4$-MSN-10 nanoparticles after adsorption of *Dunaliella salina*.

Figure 3C:
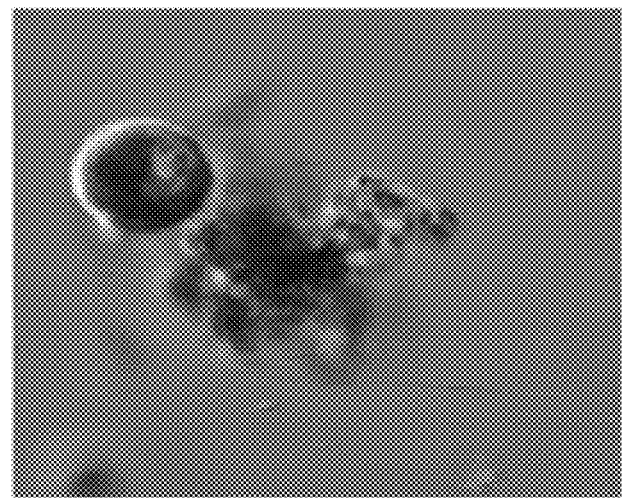

FIG. 3C is a microscope image of AP-$Fe_3O_4$-MSN-10 nanoparticles after adsorption of *Dunaliella salina*.

Figure 3D:
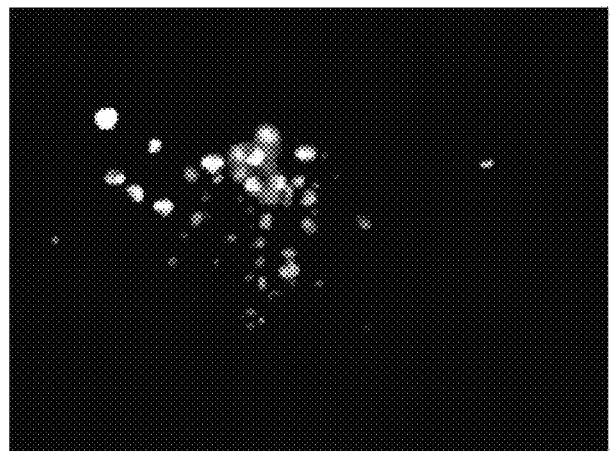

FIG. 3D is a florescent field image of AP-$Fe_3O_4$-MSN-10 nanoparticles after adsorption of *Dunaliella salina*.

Figure 3E:

FIG. 3E is a florescent field image of AP-$Fe_3O_4$-MSN-10 nanoparticles after adsorption of *Dunaliella salina*.

Figure 3F:
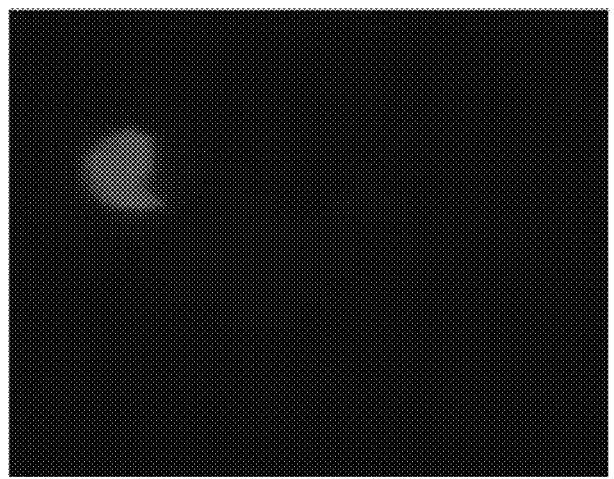

FIG. 3F is a florescent field image of AP-$Fe_3O_4$-MSN-10 nanoparticles after adsorption of *Dunaliella salina*.

Figure 4:
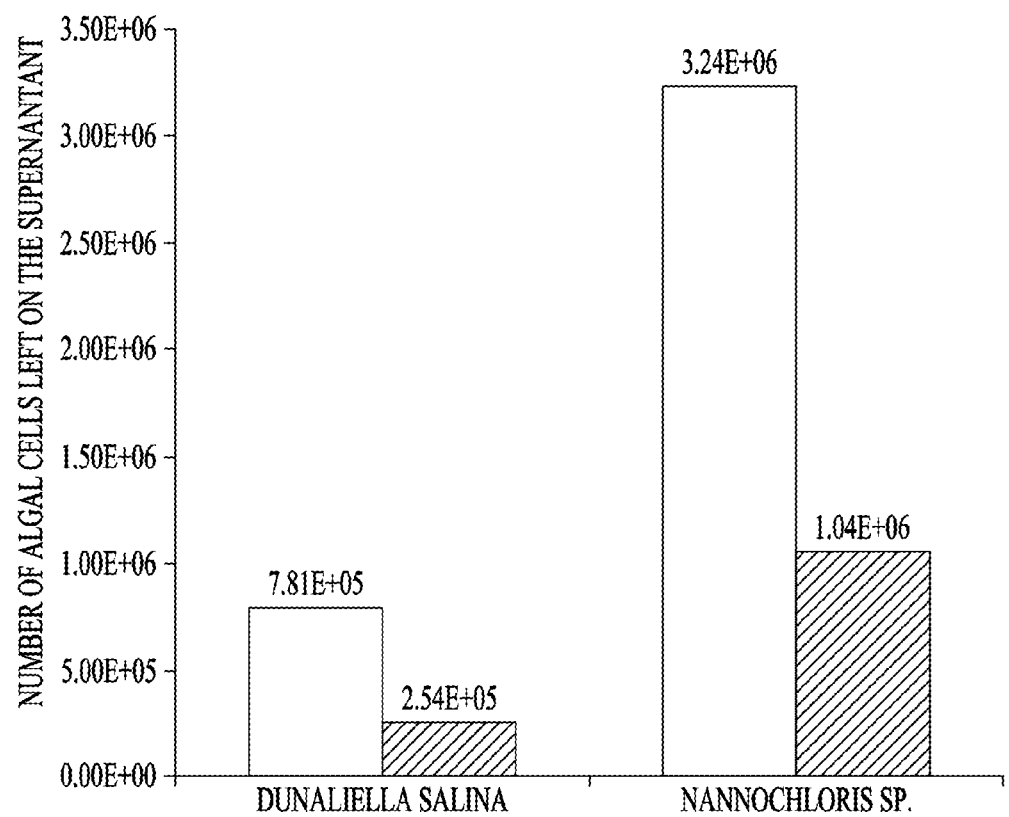

FIG. 4 is a graph of the number of algal cells remaining in the supernatant after adsorption using AP-$Fe_3O_4$-MSN-10 nanoparticles.

Figure 5:
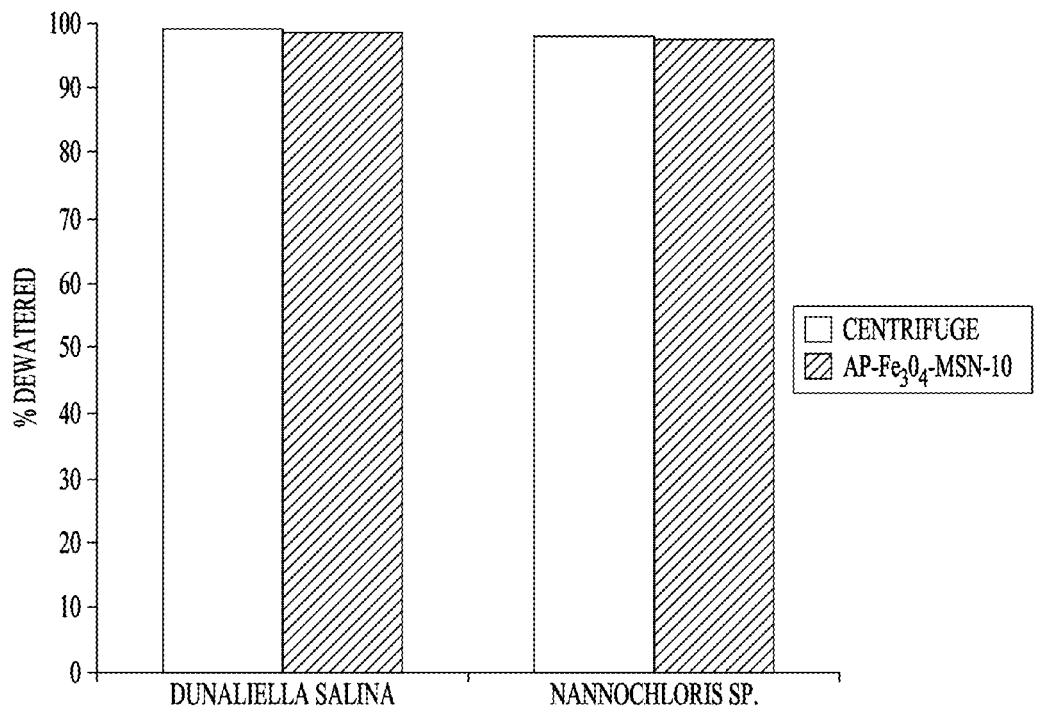

FIG. 5 is a graph of the percentage of algae dewatered after adsorption of algae by AP-$Fe_3O_4$-MSN-10 nanoparticles.

Figure 6:
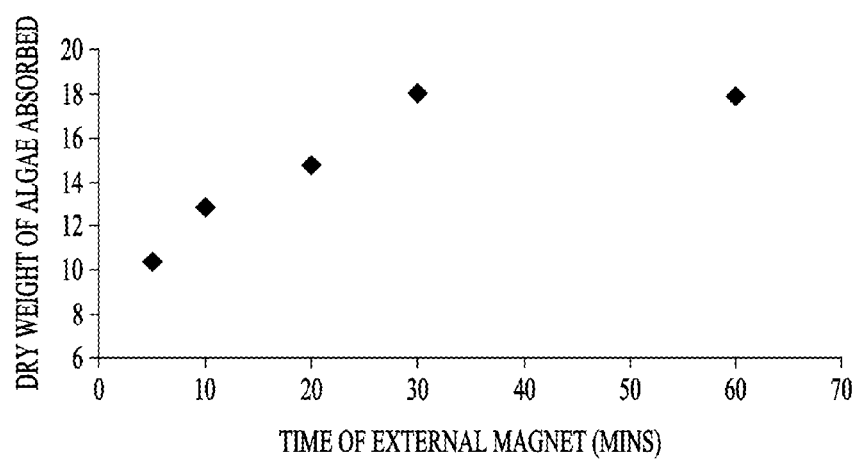

FIG. 6 illustrates the dry weight of algae adsorbed versus the amount of time AP-$Fe_3O_4$-MSN-10 nanoparticles were exposed to a magnetic field.

DETAILED DESCRIPTION

Reference will now be made in detail to certain claims of the disclosed subject matter, examples of which are illustrated in the accompanying drawings. While the disclosed subject matter will be described in conjunction with the enumerated claims, it will be understood that they are not intended to limit the disclosed subject matter to those claims. On the contrary, the disclosed subject matter is intended to cover all alternatives, modifications, and equivalents, which can be included within the scope of the presently disclosed subject matter as defined by the claims.

References in the specification to "one embodiment," "an embodiment," "an example embodiment," etc., indicate that the embodiment described can include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

Values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a concentration range of "about 0.1% to about 5%" should be interpreted to include not only the explicitly recited concentration of about 0.1 wt % to about 5 wt %, but also the individual concentrations (e.g., 1%, 2%, 3%, and 4%) and the sub-ranges (e.g., 0.5%, 1.1%, 2.2%, 3.3%, and 4.4%) within the indicated range.

In this document, the terms "a," "an," or "the" are used to include one or more than one unless the context clearly dictates otherwise. The term "or" is used to refer to a nonexclusive "or" unless otherwise indicated. In addition, it is to be understood that the phraseology or terminology employed herein, and not otherwise defined, is for the purpose of description only and not of limitation. Any use of section headings is intended to aid reading of the document and is not to be interpreted as limiting; information that is relevant to a section heading may occur within or outside of that particular section. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

In the methods of manufacturing described herein, the steps can be carried out in any order without departing from the principles of the invention, except when a temporal or operational sequence is explicitly recited.

Furthermore, specified steps can be carried out concurrently unless explicit claim language recites that they be carried out separately. For example, a claimed step of doing X and a claimed step of doing Y can be conducted simultaneously within a single operation, and the resulting process will fall within the literal scope of the claimed process.

The present invention provides a magnetic mesoporous nanoparticle that includes a mesoporous silicate nanoparticle and iron oxide. The present invention also provides a method of using magnetic mesoporous nanoparticles to sequester microorganisms from a media.

The present invention provides benefits and advantages over other methods of sequestering a microorganism from a media. Depending on the embodiment of the present invention, these benefits and advantages can take many forms, and can include any combination of the following, for example: The present invention can be more efficient than other methods of sequestering microorganisms. The higher efficiency can be a use of less energy to sequester the microorganisms, or the use of less time to sequester the microorganisms, for example. The present invention can avoid the addition of soluble chemicals to the media, which some methods require to facilitate the sequestration. The addition of soluble chemicals can sometimes prevent the facile reuse or consumption of the media, and can kill the microorganism. In some embodiments of the present invention, soluble or insoluble chemicals can be added to the water to facilitate sequestration of the microorganisms. The present invention can avoid the high-energy demands of filtration methods, which can require high pressures and tend to result in clogging of the filter necessitating a backwash or filter-cleaning procedure. In other embodiments of the present invention, the energy demands can be similar to that of filtration methods. The present invention can have less moving parts than other methods of microorganism sequestration. In some embodiments, the nanoparticles of the present invention can be reused through multiple sequestration cycles. In other embodiments, the nanoparticles of the present invention are used for one sequestration cycle.

DEFINITIONS

The term "about" as used herein can refer to a variation of ±5%, 10%, or 20% of the value specified. For example, "about 50" percent can in some embodiments carry a variation from 45 to 55 percent. For integer ranges, the term "about" can include one or two integers greater than and less than a recited integer.

The term "contacting" as used herein refers to the act of touching, making contact, or of bringing to immediate or close proximity, including at the molecular level, for example, to bring about a chemical reaction or physical change.

The term "adsorb" or "adsorption" as used herein refers to the binding of a microorganism to a nanoparticle, wherein the microorganism is reversibly or irreversibly bound to the particle. The binding can occur on the outer surface of the particle, including outer surfaces that are within the outer periphery of the particle, including the insides of pores that may be present in the nanoparticle.

The term "algae" as used herein refers to the paraphyletic group of simple, typically autotrophic, photosynthetic organisms, ranging from unicellular (e.g., green algae) to multicellular forms. Suitable algae genera can include *Botryococcus, Chlamydomas, Chlorella, Crypthecodinium, Cyclotella, Cylindrotheca, Dunaliella, Haematococcus, Isochrysis, Monallanthus, Monoraphidium, Nannochloris, Nannochloropsis, Neochloris, Nitzschia, Phaeodactylum, Schizochytrium, Spirulina, Stichococcus, Synechocystis, Tagetes*, and *Tetraselmis*. Specific species can include, for example, *Botryococcus braunii, Chlamydomas perigranulata, Chlorella emorsonii, Chlorella minutissima, Chlorella sorokiniana, Chlorella vulgaris, Crypthecodinium Cohnii, Cyclotella cryptica, Dunaliella Bardawil, Dunaliella salina, Dunaliella primolecta, Haematococcus pluvialis, Isochrysis galbana, Monallanthus salina, Neochloris oleoabundans, Nitzschia closterium, Phaeodactylum tricornutum, Spirulina platensis, Tagetes erecta, Tagetes patula, Tetraselmis suecica*, or *Tetraselmis suecica*. Algea can include any suitable form of algae, including genetically modified algae, e.g., transgenic microalgae, are well known in the art. See, for example, Leon-Banares et al., *Trends in Biotechnology*, 22 (2004) 45-52.

The term "microalgae" as used herein refers to microscopic algae, typically found in freshwater and marine systems, often referred to as microphytes.

As used herein, the term "sequestering" or "sequestration" of a microorganism, such as microorganism from water, refers to the process of concentrating a microorganism. The concentration can occur by, for example, adsorbing and/or adsorbing the microorganism (e.g., algae) onto or into a nanoparticle. The adsorbing or adsorbing can include binding to the surface of the nanoparticle, such as by electrostatic associations, and the like.

The term "organic pigment" as used herein refers to one or more of 13-carotene, astaxanthin, zeaxanthin, a carotenoid or a chlorophyll, or another organic dye, for example, found in microorganisms.

The term "organic solvent" as used herein refers to a carbon containing liquid that dissolves certain organic compounds. A "hydrophobic organic solvent" refers to an organic solvent that is substantially water-immiscible, as is understood by those of skill in the art. Hydrophobic organic solvents include, but are not limited to carbon tetrachloride, chloroform, cyclohexane, 1,2-dichloroethane, dichloromethane, diethyl ether, dimethyl formamide, ethyl acetate, heptane, hexane, methyl-tert-butyl ether, pentane, toluene, or 2,2,4-trimethylpentane. Aliphatic hydrocarbons such as hexanes and petroleum ethers have been found to be especially suitable for use in the extractions described herein.

As used herein, an "aqueous medium" or "culture broth" can be any water-containing environment that can support the life cycle of microorganisms. An aqueous medium can be a gel that includes about 0.01% to about 5% dry solids and about 95% to about 99% moisture, e.g., water. An aqueous medium can also be a fermentor for microorganisms, or a natural environment for microorganisms, such as a pool or pond.

The term "nanoparticles" as used herein refers to particles with an average diameter less than about 750 nm. In some embodiments, the particles can be less than about 500 nm, or less than about 300 nm, or approximately 50-200 nm. In some embodiments, nanoparticles can be approximately 75-100 nm in diameter.

The term "mesoporous" as used herein refers to containing pores wherein the pores have a diameter of between about 0.5 nm and about 200 nm, or between about 1 nm and about 100 nm, or between about 2 nm and about 50 nm.

The term "adsorption cycle" as used herein refers to adsorbing a microorganism to a nanoparticle, separating the nanoparticle from the media, and separating the microorganism from the nanoparticle.

Magnetic Mesoporous Nanoparticle

The present invention provides a magnetic mesoporous nanoparticle. The magnetic mesoporous nanoparticle includes a mesoporous silicate nanoparticle. The magnetic mesoporous nanoparticle also includes iron oxide. The magnetic mesoporous nanoparticle is magnetic. The magnetic mesoporous nanoparticle has a mesoporous structure.

The magnetism exhibited by the nanoparticle can be any kind of magnetism that allows the particle to be drawn in a particular direction by the effect of a magnetic field. The magnetism can include diamagnetism, paramagnetism, ferromagnetism, antiferromagnetism, ferrimagnetism, and superparamagnetism.

The iron oxide can be any iron oxide known to one of skill in the art that can give magnetic properties to a nanoparticle, where in some embodiments the magnetic properties occur after further processing. Further processing can include reduction or oxidation of the iron oxide after inclusion in a nanoparticle. The iron oxide is preferably selected from $Fe_3O_4$ and $Fe_2O_3$, and is most preferably $Fe_3O_4$.

The magnetic mesoporous nanoparticle can include an adsorbed microorganism, wherein the microorganism is adsorbed to the pores or surface of the magnetic mesoporous nanoparticle. The microorganism can be any microorganism known to one of skill in the art. Examples of microorganisms can include unicellular or multicellular organisms, and can include prokaryotes such as bacteria and archaea, and eukaryotes such as protists, fungi, plants, fungi, and animals. The microorganism can be algae. The algae can be microalgae.

The nanoparticle can include one or more amino($C_1$-$C_{20}$) alkyl groups with alkyl units covalently bound to the nanoparticle, wherein the $C_1$-$C_{20}$ alkyl groups are optionally interrupted by one or two —NH— groups. In some embodiments, the $C_1$-$C_{20}$ alkyl groups are not interrupted by one or two —NH— groups. The amino($C_1$-$C_{20}$)alkyl groups on a given nanoparticle can all have approximately the same length ($C_1$-$C_{20}$)alkyl group, or alternatively can have of different lengths. Likewise, if an —NH— group interrupts an amino($C_1$-$C_{20}$) alkyl group, there can be the same number of —NH— groups interrupting each alkyl group, and there can be an —NH— group interrupting the alkyl group at the same location of the alkyl group, for all amino($C_1$-$C_{20}$)alkyl groups on a given nanoparticle. Also, —NH— groups can interrupt alkyl groups in varying numbers and location for all amino($C_1$-$C_{20}$) alkyl groups on a given nanoparticle. Embodiments of the present invention encompass any density of amino($C_1$-$C_{20}$) alkyl groups on the nanoparticles, such that the nanoparticle can adsorb a microorganism.

In some embodiments, the nanoparticle can have a diameter of approximately 150 nm to approximately 1200 nm. The nanoparticle can have a diameter of 300 nm to approximately 600 nm. The nanoparticle can have a surface area of approximately 100 $m^2$/g to approximately 1000 $m^2$/g, or the nanoparticle can have a surface area of approximately 200 $m^2$/g to approximately 500 $m^2$/g. The nanoparticle can have a pore size of approximately 1 nm to approximately 20 nm. The nanoparticle can have a pore size of approximately 5 nm to approximately 15 nm. The nanoparticle can have a pore size of approximately 7.5 nm to approximately 10 nm.

In some embodiments, the nanoparticle can selectively adsorb one microorganism over another microorganism. For the adsorption to be selective, the selectivity does not need to be completely exclusive. For example, if in a 1:1 mixture of microorganism A and microorganism B, a plurality of nanoparticles adsorb 48% microorganism A and 52% microorganism B, the nanoparticles can be said to be selective toward adsorption of microorganism B. Also, if in a 1:1 mixture of microorganism A and microorganism B, a plurality of nanoparticles adsorb 25% microorganism A and 75% microorganism B, the nanoparticles can be said to be selective toward adsorption of microorganism B. Also, if in a 1:1 mixture of microorganism A and microorganism B, a plurality of nanoparticle adsorb 1% microorganism A and 99% microorganism B, the nanoparticles can be said to be selective toward adsorption of microorganism B. In any one of these examples of selectivity one or more other microorganisms or microorganism-sized materials can be present, and similarly the nanoparticles can be selective against adsorption of any one or more of the other microorganisms or microorganism-sized materials and selective towards adsorption of microorganism A or B.

The physical characteristics of the nanoparticle can be selected to encourage the type of selective microorganism adsorption described above. Characteristics of the nanoparticle that can be selected to encourage selective adsorption include any characteristic that can alter the adsorption selectivity of the nanoparticle, for example the pore size, pore spacing, surface area, chemical functionality, and the nanoparticle diameter. In some embodiments, nanoparticles with a mixture of characteristics may be desired to most effectively selectively adsorb one or more microorganisms.

Mesoporous silicate nanoparticles (MSNs) can be prepared as the first step in the preparation of a magnetic mesoporous nanoparticle. MSNs and their preparation are described in, for example, U.S. Patent Application Publication Nos. 2006/0154069 (Lin et al.), 2006/0018966 (Lin et al.), or Linton et al., *Chem. Mater.* 2008, 20, 2878-2880. The mesoporous silicate nanoparticle is any suitable mesoporous silicate nanoparticle, as is known to one of skill in the art. The mesoporous silicate nanoparticle includes repeating —O—Si(R)$_2$— units, which form a silicate matrix. The R group can independently designate any suitable substituent, including for example, siloxy, alkoxy, halo, or alkyl, wherein alkoxy or alkyl can be for example $C_1$-$C_{20}$ branched or straight chain. The repeating —O—Si(R)$_2$— units can be bound to any other suitable unit in the matrix. For example, an —O—Si(R)$_2$— unit can be bound directly to another silicon atoms, forming an —O—Si(R)$_2$—O— unit. In another example, an —O—Si(R)$_2$— unit can be bound to an alkoxy group, which can in turn be bound to any suitable substituent, such as a silicon atom-containing substituent, such as another —O—Si(R)$_2$— unit for example. Any suitable procedure can be used to generate the mesoporous silicate nanoparticle. In some examples, a mesoporous silicate nanoparticle can be made by condensing an alkoxysilane. In some examples, the alkoxysilane can be tetramethylorthosilicate (TMOS), tetraethylorthosilicate (TEOS), tetrakis(2-hydroxyethyl)orthosilicate (THEOS), methyldiethoxysilane (MDES), 3-(glycidoxypropyl)triethoxysilane (GPTMS), 3-(trimethyoxysilyl)propylacrylate (TMSPA), N-(3-triethoxysilylpropyl)pyrrole (TESPP), vinyltriethyoxysilane (VTES), methacryloxypropyltriethoxysilane (TESPM), diglycerylsilane (DGS), methyltriethoxysilane (MTMOS), trimethylmethoxysilane (TMMS), ethyltriethoxysilane (TEES), n-propyltriethoxysilane (TEPS), n-butyltriethyoxysilane (TEBS), 3-aminopropyltriethoxysilane (APTS), 2-(2,4-dinitrophenylamino)propyltriethoxysilane, mercaptopropyltriethoxysilane (TEPMS), 2-(3-aminoethylamino)propyltriethoxysilane, isocyanatopropyltriethoxysilane, hydroxyl-terminated polydimethylsiloxane, triethoxysilyl-terminated polydimethylsiloxane, methyltriethoxysilane (MTES), or triethoxysilyl-terminated poly(oxypropylene).

In some embodiments, acid or base treatment can allow hydrolysis of the alkoxysilane to give a reactive silanol, which can then react with other alkoxysilanes or silanols (e.g. to form —Si(R)$_2$—O—Si(R)$_2$— units) or with other reactive groups. In some embodiments, a reactive silanol can be provided by treatment of silica (e.g. $SiO_2$) with acid or base. Hydroxyl groups (e.g. R'—OH, wherein R' is any suitable substituent of suitable valancy, e.g. monovalent or divalent) from other compounds can condense with alkoxysilanes or silanols to give substituted silicones (e.g. —Si(R)$_2$—O—R'). Any suitable compound (e.g. silicon-containing or non-silicon containing) having any suitable number of hydroxyl or alkoxy groups (e.g. 1, 2, 3, 4, or more) can participate in the condensation, such that a wide variety of structures are possible for the mesoporous silicate nanoparticle. For example, polyols can condense with multiple alkoxysilanes or silanols to give cross-linking of silicon atoms, e.g. HO—R'—OH can give —Si(R)$_2$—O—R'—O—Si(R)$_2$— units. Examples of suitable polyols can include any polyol that includes $C_{1-10}$ repeating alkylene oxide units, including polyols with more than one different $C_{1-10}$ repeating unit (e.g. ethylene oxide units such as in polyethylene glycol, propylene oxide units such as in propylene glycol, or a combination thereof such as in a co-polymer of ethylene and propylene glycol), wherein the polyol can have any suitable chain length or molecular weight.

As described further below, the mesoporous silicate nanoparticle can be transformed into a magnetic mesoporous nanoparticle via the addition of a magnetic iron oxide material. The iron oxide is added by contacting the mesoporous silicate nanoparticle with an iron precursor, optionally followed by a reduction or oxidation step. Thus, the magnetic mesoporous nanoparticle includes a reaction product of a mesoporous silicate nanoparticle and an iron precursor. Further, the surface of the nanoparticle can be functionalized, to give a surface-functionalized magnetic mesoporous nanoparticle, as described below.

In an embodiment, MSNs can be prepared as described in Example 1, below. The mesoporous silicates can have mesopores and have a particle size of about 50 nm to about 1 µm diameter. In one embodiment, the pores are hexagonally arranged. The pores can have any suitable arrangement. In one embodiment, the mesoporous silicates have a particle size of at least about 75 nm, 100 nm, or at least about 200 nm diameter. In another embodiment, the mesoporous silicates have a particle size of less than about 750 nm, less than about 500 nm, or less than about 300 nm diameter. In some embodiments, the spheroid particles are about 300-600 nm in diameter. The MSNs typically have a surface area of about 100 $m^2/g$ to about 600 $m^2/g$, or about 150 $m^2/g$ to 550 $m^2/g$, or about 200 $m^2/g$ to about 500 $m^2/g$. The average pore diameter can be about 5 nm to about 15 nm, or about 7.5 nm to about 10.5 nm for standard mesoporous particles. The average pore volume can be about 0.1 $cm^3/g$ to about 6 $cm^3/g$, or about 0.25 $cm^3/g$ to about 3 $cm^3/g$, or about 0.5 $cm^3/g$ to about 1.5 $cm^3/g$.

As conventionally prepared, MSNs are spherical, but they can also been prepared under conditions that yield other shapes such as rods. The particles can include mesoporous silicates of any shape, provided the shape and other associated features are suitable for adsorbing and/or adsorbing microorganisms.

The MSNs can be transformed into magnetic mesoporous silicate nanoparticles, for example, as described in Example 2 below. The mesoporous silicate nanoparticle can be contacted with an iron precursor, followed by an optional reduction or oxidation step, to give a magnetic mesoporous nanoparticle. The iron precursor can be any suitable iron precursor. For example, the iron precursor can be $Fe(NO_3)_3$, including $Fe(NO_3)_3 \cdot 9H_2O$. Other examples include $(NH_4)_2Fe(SO_4)_2$, $NH_4Fe(SO_4)_2$, $FeO$, $Fe_3O_4$, $Fe_2O_3$, $FeOCl$, $FeS$, $Fe(OAc)_2$, $FeX_2$ or $FeX_3$ wherein X is independently chloro, bromo, or fluoro, $Fe_3(PO_4)_2$, $FeSO_4$, $FeTiO_3$, $Fe(NO_3)_3$, and the like, or any hydrate thereof. The reduction or oxidation is an optional step; in some embodiments, a reduction or oxidation is performed, while in other embodiments, a reduction or oxidation is not performed. The reduction or oxidation can be performed via any suitable means. In some examples, the reduction can be performed via application of $H_2$ gas. In some examples, the $H_2$ can be applied with heating.

Magnetic mesoporous silicate nanoparticles, such as $Fe_3O_4$-MSN-10, typically have a particle size of about 50 nm to about 1 µm. In one embodiment, the magnetic mesoporous silicate nanoparticles have a particle size of at least about 75 nm, 100 nm, or at least about 200 nm. In another embodiment, the magnetic mesoporous silicate nanoparticles have a particle size of less than about 750 nm, less than about 500 nm, or less than about 300 nm. In some embodiments, the spheroid particles are about 300-600 nm in diameter. The magnetic mesoporous silicate nanoparticles typically have a surface area of about 100 $m^2/g$ to about 600 $m^2/g$, or about 150 $m^2/g$ to 550 $m^2/g$, or about 200 $m^2/g$ to about 500 $m^2/g$. The average pore diameter can be about 5 nm to about 15 nm, or about 7.5 nm to about 10.5 nm. The average pore volume can be about 0.1 $cm^3/g$ to about 6 $cm^3/g$, or about 0.25 $cm^3/g$ to about 3 $cm^3/g$, or about 0.5 $cm^3/g$ to about 1.5 $cm^3/g$.

The magnetic mesoporous silicate nanoparticles can be amine-functionalized, for example, as described in Example 3 below. Amine-functionalized mesoporous nanoparticles, such as AP-$Fe_3O_4$-MSN-10, typically have a particle size of about 50 nm to about 1 µm. In one embodiment, the amine-functionalized mesoporous nanoparticles have a particle size of at least about 75 nm, 100 nm, or at least about 200 nm. In another embodiment, the amine-functionalized mesoporous nanoparticles have a particle size of less than about 750 nm, less than about 500 nm, or less than about 300 nm. In some embodiments, the amine-functionalized mesoporous nanoparticles are about 300-600 nm in diameter. The amine-functionalized mesoporous nanoparticles typically have a surface area of about 100 $m^2/g$ to about 600 $m^2/g$, or about 150 $m^2/g$ to 550 $m^2/g$, or about 200 $m^2/g$ to about 500 $m^2/g$. The average pore diameter can be about 5 nm to about 15 nm, or about 7.5 nm to about 10.5 nm. The average pore volume can be about 0.1 $cm^3/g$ to about 6 $cm^3/g$, or about 0.25 $cm^3/g$ to about 3 $cm^3/g$, or about 0.5 $cm^3/g$ to about 1.5 $cm^3/g$.

In an example, the properties of MSN-10 mesoporous silicate nanoparticles, $Fe_3O_4$-MSN-10 magnetic mesoporous silicate nanoparticles, and AP-$Fe_3O_4$-MSN-10 amine-functionalized mesoporous nanoparticles, are as follows:

|  | Surface area ($m^2/g$) | Pore volumes ($cm^3/g$) | Pore diameters (nm) |
| --- | --- | --- | --- |
| MSN-10 | 451 | 1.2 | 9.8 |
| $Fe_3O_4$-MSN-10 | 356 | 0.9 | 9.2 |
| AP-$Fe_3O_4$-MSN-10 | 229 | 0.6 | 7.9 |

Method of Sequestration of Microorganisms

The present invention also provides a method of using magnetic mesoporous nanoparticles to sequester a microorganism from a media. The method includes contacting a mixture including one or more microorganisms and a media with a plurality of magnetic mesoporous nanoparticles. The magnetic mesoporous nanoparticles can be any magnetic mesoporous nanoparticle effective for sequestration of microorganisms, and can include, for example, the magnetic mesoporous nanoparticles described above. The contacting is sufficient to adsorb the microorganisms to the pores or surface of the magnetic mesoporous nanoparticles. The method also includes exposing the nanoparticles to a magnetic field. The exposure to the magnetic field is sufficient to concentrate the adsorbed microorganism.

The media can be any material that can form a mixture with the microorganism. The media is preferably aqueous. The media can be at least about 5%, 25%, 50%, 75%, or at least 99% water. The media can be an organic solvent. The media can be any mixture of water with an organic solvent, including emulsions or mixtures that form multiple layers.

In the method, the microorganism can be any microorganism. In one preferred embodiment, the microorganism is algae. The method can include selectively adsorbing one or several microorganisms over one or more than one other microorganism. The characteristics of the nanoparticle can be chosen to encourage the type of selective adsorption desired.

The method can be performed using any suitable volume of media, e.g. about 1 mL or less to about 1 L, or about 1 L to about 1000 L, or using a volume exceeding 1000 L. The media can contain any suitable concentration of microorganisms. In some embodiments, the method is particularly efficient when used to separate large quantities of microorganisms from media, compared to other methods.

The nanoparticles and the microorganism can be exposed to one another at any relative concentration, and for any duration of time, sufficient to allow formation of at least some microorganism-adsorbed nanoparticles. For example, the duration of time can be 1 minute, 5 minutes, 10 minutes, 20 minutes, 30 minutes, 60 minutes, 4 hours, or 8 hours.

The magnetic field can be generated in any effective method known to one of skill in the art, and can be of any strength sufficient to concentrate the adsorbed microorganisms. The magnetic field can be generated by an electromagnet, a non-electromagnet, or a combination thereof. The magnetic field can originate from a source that is in contact with the media, or from a source that is outside the approximate boundaries of the media. The magnetic field can originate from multiple sources, and the multiple sources can be in different locations.

The exposure to the magnetic field is sufficient to concentrate the microorganism. Concentration refers to the amount of microorganisms in a given volume of the media, and can refer to any degree of concentration. Concentration can include an at least 0.01%, 5%, 10%, 20%, 40%, 80%, 90%, 95%, 99% increase in the amount of microorganism in a given volume of the media. Concentrating the microorganisms can also include removing the adsorbed microorganisms from the media, which corresponds to the given volume of the media approaching zero as the amount of the microorganism remains constant. Concentrating the microorganisms can refer to the effect of the magnetic field on any number of nanoparticles with adsorbed microorganisms, including all of the nanoparticles, nearly all the nanoparticles, some of the nanoparticles, a few of the nanoparticles, or one of the nanoparticles with adsorbed microorganisms. The nanoparticles without adsorbed microorganisms can be equally affected by the applied magnetic field. The exposure to the magnetic field can be sufficient to move the nanoparticles towards the magnetic field. The exposure to the magnetic field can be sufficient to move the nanoparticles away from the magnetic field. The exposure can be sufficient to induce a magnetic field in each exposed nanoparticle. The exposure can be sufficient to cause the nanoparticles to move toward or away from a specific direction. The exposure can be sufficient to cause the nanoparticles to gather in a specific area.

In some embodiments, contacting the mixture with the nanoparticles causes flocculation of the nanoparticles, including nanoparticles with adsorbed microorganisms, nanoparticles without adsorbed microorganisms, or both. The contacting can cause flocculation of the adsorbed microorganisms. The contacting can cause flocculation of both the nanoparticles and the adsorbed microorganisms. Flocculation of the nanoparticles or the adsorbed microorganisms can cause co-flocculation of unadsorbed microorganisms. Co-flocculation can allow non-adsorbed microorganisms to be affected by the magnetic field in a manner similar to the adsorbed microorganisms, due to their flocculation therewith.

In some embodiments, the method further provides separating the magnetic mesoporous nanoparticles with an adsorbed microorganism from the media. The separation can be conducted in any effective method known to one of skill in the art, including transferring the media away from the microorganisms, transferring the microorganisms away from the media, decanting, draining, centrifuging, siphoning, pumping, gravity, or a combination thereof.

The method can remove any reasonable number of the desired microorganisms from the media. In some embodiments, the method removes at least 99% of the microorganisms from the media. In other embodiments, the method removes at least 95%, 90%, 80%, 60%, 40%, 20%, 10%, 5%, or at least 1% of the desired microorganisms from the media. In some embodiments, it can be more efficient to not remove all of the microorganism from the media in an adsorption cycle.

The method can further provide desorbing the adsorbed microorganism from the magnetic mesoporous nanoparticles with the adsorbed microorganism. Desorption can occur in any effective manner known to one of skill in the art. For example, desorption can be elicited by washing the nanoparticles with adsorbed microorganisms. The liquid used to wash the nanoparticles can be an organic solvent. The liquid can be water, an organic solvent, or a mixture thereof. The liquid can have another compound dissolved therein to facilitate the desorption process. The washing can be gentle with normal pressure and temperature. Alternatively, the washing can be vigorous with any one of scrubbing, pressing, freezing, heating, high pressure washing, grinding, acid or base treatment, pressurized air treatment, or a combination thereof.

In one example, desorption can be elicited by applying heat to the adsorbed microorganisms. The amount of heat can be sufficient to denature, at least partially, the surface structure of the microorganisms, which can alter the interaction between the nanoparticles and the microorganisms. The heat can be applied in any manner known to one of skill in the art. The nanoparticles can be in a liquid when heat is applied to effect desorption, such as water, and organic solvent, or a mixture thereof. The nanoparticles can be dry or substantially dry when heat is applied to effect desorption. The nanoparticles can be in any medium known to one of skill in the art when the heat is applied.

Any method of altering the interaction between the adsorbed microorganisms and the magnetic mesoporous nanoparticles can be used to effect desorption. The method used to alter the interactions between the nanoparticle and the adsorbed microorganisms can include sonication, agitation, heating, cooling, addition or removal of solvent, addition of a chemical compound, other methods known to one of skill in the art, or any combination thereof. For example, placing the nanoparticle-microorganism aggregate in a particular solvent can alter the interactions sufficiently to effect desorption. An organic solvent can be an example of a solvent that can alter interactions between the adsorbed microorganisms and the particles, but any solvent or medium known to one of skill in the art can be used. In one example, sonication in the presence of nonpolar organic solvents, e.g. hexanes or the like, can effect efficient desorption of the microorganisms from the nanoparticles. In another example, the microorganisms can be lysed by any method known to one of skill in the art to alter the interaction between the microorganism and the magnetic mesoporous nanoparticle and effect desorption.

In another example, magnetic mesoporous nanoparticles with adsorbed microorganisms can be subjected to lysing to release the contents of the microorganisms into solution, the solution containing the contents of the microorganisms can be removed, and the nanoparticles that still have remnants of the microorganisms attached can be cleaned by any method known to one of skill in the art, making them ready for reuse as microorganism-adsorbing magnetic mesoporous nanoparticles. The cleaning method can include, for example, agitation, chemical treatment, or a combination thereof.

The method can also further provide separating the desorbed microorganism from the particles. The method of desorption can inherently separate the desorbed microorganisms from the particles. In other embodiments, the separation of the desorbed microorganisms occurs in a separate step, wherein the separation occurs by any effective manner known to one of skill in the art. The separation can include lysing, washing, sifting, air pressure treatments, treatment with solvents, or a combination thereof.

In some embodiments, the microorganism lives through the process of being adsorbed, separated from the media, and desorbed. In some embodiments, at least approximately 99%, 95%, 90%, 80%, 60%, 40%, 20%, 10%, 5%, or 1% of the microorganisms adsorbed and separated survive. In some embodiments, very few, of the microorganisms adsorbed, separated from the media, and desorbed from the nanoparticle, survive. In some embodiments none of the microorganisms survive.

In some embodiments, after desorbing the microorganisms from the magnetic mesoporous nanoparticles and separating the desorbed microorganisms from the nanoparticles, the magnetic mesoporous nanoparticles can be reused for another adsorption cycle. In some embodiments, the nanoparticles can be reused at least 2 times, 3 times, 5 times, 10 times, 20 times, 50 times, or at least 100 times.

In some embodiments, the media from which the microorganisms were separated can be used for particular purposes. For example, water separated from algae can be used to culture algae. In another example, water separated from algae can be used for drinking water. The media can be used with or without further processing, depending on the purity needs of the use.

The desorbed microorganisms can be lysed by chemical or physical means, by any method known to one of skill in the art. The lysing of the microorganisms can cause the internal chemicals of the microorganisms to spill out into the solution, where they can conveniently be processed. Processing can include separation and purification of the molecules of interest.

In a specific embodiment, the present invention provides a method of using magnetic mesoporous nanoparticles to sequester algae from water. The method includes contacting a mixture including one or more algae and water with one or more magnetic mesoporous nanoparticle. The magnetic mesoporous nanoparticle includes a mesoporous silicate nanoparticle and $Fe_3O_4$. The contacting is sufficient to adsorb the algae to the pores or surface of the magnetic mesoporous nanoparticles. The method further includes exposing the magnetic mesoporous nanoparticle with the adsorbed algae to a magnetic field. The exposure to the magnetic field is sufficient to concentrate the adsorbed microorganisms. In some embodiments, the method further provides separating the magnetic mesoporous nanoparticles with the adsorbed algae from the water. The method can further provide separating the desorbed algae from the magnetic mesoporous nanoparticles. The method can further provide reusing the magnetic mesoporous nanoparticles for another adsorption cycle.

FIG. 1 illustrates the dry weight of the algaes *Dunaliella salina* and *Nannochloris* sp. adsorbed on 2 mg of AP-$Fe_3O_4$-MSN-10 nanoparticles for 30 minutes. An example of the synthesis of AP-$Fe_3O_4$-MSN-10 nanoparticles (amine-functionalized iron oxide mesoporous silicate nanoparticles) is given below in Examples 1-3. As shown in FIG. 1, for adsorption of both *Dunaliella salina* and *Nannochloris* sp, of the particles compared in this experiment, AP-$Fe_3O_4$-MSN-10 had the best adsorption ability. For *Nannochloris* sp, 2 mg of AP-$Fe_3O_4$-MSN-10 adsorbed 18.1 mg of dry weight algae. When the nanoparticles without amine-functionalization were used ($Fe_3O_4$-MSN-10), the adsorption decreased by 3 fold to 6.6 mg. Furthermore, iron oxide nanoparticles ($Fe_3O_4$) adsorbed 9.9 mg of dry weight algae, whereas the amine-functionalized iron oxide nanoparticles (AP-$Fe_3O_4$) adsorbed 11.6 mg of dry weight algae. Without being bound to any particular theory of operation, this data can indicate that the higher surface area of mesoporous silicate nanoparticles and the amine-functionalization are important for higher adsorption of algae.

FIG. 2 shows stills from a movie after adsorption of *Dunaliella salina* by 2 mg of AP-$Fe_3O_4$-MSN-10. In FIG. 2, the left cuvette is the control and the right cuvette shows algae sequestration using an external magnet. The left cuvette had the same concentration of algae, but nanoparticles were not added. In FIG. 2A, the placement of a magnet proximate to the cuvette is shown. In FIG. 2B, the effect of application of the magnetic field for 30 minutes is shown. In FIG. 2C, the effect of application of the magnetic field for 30 minutes is shown, from a different perspective than FIG. 2B. The inset pictures in FIGS. 2B and 2C are nanoparticles with adsorbed algae that were removed from the cuvette using a magnet in an NMR tube. The inset pictures demonstrate that the attraction between the nanoparticle-microorganism and a magnet can be stronger than capillary forces between water and the particles.

FIG. 3 shows microscope images of AP-$Fe_3O_4$-MSN-10 after the adsorption of *Dunaliella salina*. FIG. 3A shows a bright field image of AP-$Fe_3O_4$-MSN-10 after the adsorption of algae. FIGS. 3B and 3C show a confocal image of AP-$Fe_3O_4$-MSN-10 after the adsorption of algae. FIGS. 3D, 3E, and 3F show a fluorescent image of AP-$Fe_3O_4$-MSN-10 after the adsorption of algae.

FIG. 4 is a graph of the number of algal cells remaining in the supernatant after adsorption using AP-$Fe_3O_4$-MSN-10 particles. After adsorption of algae on AP-$Fe_3O_4$-MSN-10, the supernatant was processed for flow cyclometry experiments to calculate the number of algae cells that did not get adsorbed. As shown in FIG. 4, 32.5% of *Dunaliella salina* and 32.1% of *Nannochloris* sp remained in the supernatant. This indicates that 67.5% *Dunaliella sauna* and 67.9% of *Nannochloris* sp were adsorbed by 2 mg of AP-$Fe_3O_4$-MSN-10 particles over 30 minutes, respectively.

FIG. 5 is a graph of the percentage of algae dewatered after a 30 minute adsorption of algae by AP-$Fe_3O_4$-MSN-10 particles. The percentage dewatered was calculated and compared to the percentage dewatered using a conventional centrifuge. FIG. 5 shows that for embodiments of the present invention, there can be a minimal difference between the percentage dewatered using the nanoparticles compared to that obtained using a conventional centrifuge.

FIG. 6 is a graph showing the dry weight of *Nannochloris* sp adsorbed AP-$Fe_3O_4$-MSN-10 nanoparticles versus the amount of time the nanoparticles were exposed to a magnetic field. Measurements were taken at 5, 10, 20, 30, and 60 minutes. The data shows that the for this particular type of algae and this particular type of nanoparticle, the amount of algae adsorbed plateaus at around 30 minutes.

EXAMPLES

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

Example 1

Synthesis of Mesoporous Silicate Nanoparticles MSN-10

MSN-10 nanoparticles were prepared using a nonionic block co-polymer Pluronic P104 surfactant. For a typical synthesis, P104 (7 g) was dissolved in a solution containing $H_2O$ (164 g) and 4M HCl (109 g) at 55° C. under constant stirring for an hour. Tetramethylorthosilicate (10.64 g, "TMOS") was added to the surfactant solution and the mixture was stirred for 24 hours at 55° C. The reaction mixture was then transferred into a Teflon-lined autoclave and heated at 150° C. for 24 hours. The resultant white precipitate was filtered, washed with methanol, and dried in air. The surfactant was removed by calcining in air at 550° C. for 6 hours.

Example 2

Synthesis of $Fe_3O_4$-MSN-10

Iron(III) nitrate ($Fe(NO_3)_3.9H_2O$) was used as the iron precursor. The iron(III) nitrate (1.26 g) was completely dissolved in ethanol (10 ml) and then MSN-10 particles (0.5 g) were suspended in the $Fe(NO_3)_3$/ethanol solution. The suspension was left to dry in air at 30° C. with constant stirring. The solid was then calcined in air at a heating rate of 10° C. per minute from to 300° C. The resulting brownish powder was denoted as $Fe_2O_3$-MSN-10. $Fe_2O_3$-MSN-10 was reduced by calcining in a constant flow of $H_2$ (1.67 mL/s) at 300° C. for 5 hours, giving $Fe_3O_4$-MSN-10, a black powder.

Example 3

Synthesis of Amine-Functionalized $Fe_3O_4$-MSN-10 (AP-$Fe_3O_4$-MSN-10)

Amine-functionalized $Fe_3O_4$-MSN-10 was prepared by grafting 3-aminopropyltrimethoxysilane (1.5 mmol, "APTMS") to the surface of $Fe_3O_4$-MSN-10 (1 g) in refluxing toluene (100 mL) for 24 hours. The resulting AP-$Fe_3O_4$-MSN-10 particles were separated by magnetic decantation using external neodymium magnet, washed with methanol, and dried under vacuum for 24 hours.

Example 4

Adsorption of Algae by AP-$Fe_3O_4$-MSN-10

AP-$Fe_3O_4$-MSN-10 (2 mg) was dispersed in PBS buffer (2.5 ml, pH 7.4) by sonication for half hour. To this solution, *Nannochloris* sp (5 mL, algae with a cell wall) was added and the algae mixture was shaken for half hour. After half hour, the AP-$Fe_3O_4$-MSN-10 along with adsorbed algae was captured by external magnet and dried in oven at 100° C. to calculate the adsorbed dry weight of algae. A flow cytometry experiment was conducted on supernatant to count the number of algae cells that were not adsorbed. A similar experiment was conducted for *Dunaliella salina* (algae without a cell wall). As control experiments, similar procedure was repeated using $Fe_3O_4$-MSN-10 nanoparticles, $Fe_3O_4$ nanoparticles, and amine-functionalized $Fe_3O_4$ nanoparticles.

Example 5

Effect of External Magnetic Field Time

AP-$Fe_3O_4$-MSN-10 (2 mg) was dispersed in PBS buffer (2.5 ml, pH 7.4) by sonication for half hour. To this solution, *Nannochloris* sp (5 mL, algae with a cell wall) was added and the algae mixture was shaken for half hour. The adsorbed algae-material composite was captured using external magnet for 5, 10, 20, 30 and 60 minutes. The composite was dried in oven at 100° C. overnight and the adsorbed dry weight of algae was calculated.

The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Additional Embodiments

The present invention can be illustrated by the following non-limiting embodiments, the numbering of which is not to be construed as designating levels of importance:

Embodiment 1 provides a magnetic mesoporous nanoparticle, including: a mesoporous silicate nanoparticle; and iron oxide; wherein the magnetic mesoporous nanoparticle is magnetic; wherein the magnetic mesoporous nanoparticle has a mesoporous structure.

Embodiment 2 provides the magnetic mesoporous nanoparticle of Embodiment 1, further including at least one microorganism, wherein the microorganism is adsorbed to the pores or surface of the magnetic mesoporous nanoparticle.

Embodiment 3 provides the magnetic mesoporous nanoparticle of Embodiment 2, wherein the microorganism is an algae.

Embodiment 4 provides the magnetic mesoporous nanoparticle of Embodiment 3, wherein the algae is a microalgae.

Embodiment 5 provides the magnetic mesoporous nanoparticle of any one of Embodiments 3-4, wherein the algae includes *Botryococcus, Chlamydomas, Chlorella, Crypthecodinium, Cyclotella, Cylindrotheca, Dunaliella, Haematococcus, Isochrysis, Monallanthus, Monoraphidium, Nannochloris, Nannochloropsis, Neochloris, Nitzschia, Phaeodactylum, Schizochytrium, Spirulina, Stichococcus, Synechocystis, Tagetes,* or *Tetraselmis*.

Embodiment 6 provides the magnetic mesoporous nanoparticle of any one of Embodiments 1-5, further including: one or more amino($C_1$-$C_{20}$)alkyl groups with alkyl units covalently bound to the nanoparticle, wherein the $C_1$-$C_{20}$ alkyl groups are independently optionally interrupted by one or two —NH— groups.

Embodiment 7 provides the magnetic mesoporous nanoparticle of any one of Embodiments 1-6, wherein the magnetic mesoporous nanoparticle has a diameter of approximately 150 nm to approximately 1200 nm.

Embodiment 8 provides the magnetic mesoporous nanoparticle of any one of Embodiments 1-7, wherein the magnetic mesoporous nanoparticle has a diameter of approximately 300 nm to approximately 600 nm.

Embodiment 9 provides the magnetic mesoporous nanoparticle of any one of Embodiments 1-8, wherein the magnetic mesoporous nanoparticle has a surface area of approximately 100 m$^2$/g to approximately 1000 m$^2$/g.

Embodiment 10 provides the magnetic mesoporous nanoparticle of any one of Embodiments 1-9, wherein the magnetic mesoporous nanoparticle has a surface area of approximately 200 m$^2$/g to approximately 500 m$^2$/g.

Embodiment 11 provides the magnetic mesoporous nanoparticle of any one of Embodiments 1-10, wherein the magnetic mesoporous nanoparticle has a pore size of approximately 5 nm to approximately 15 nm.

Embodiment 12 provides the magnetic mesoporous nanoparticle of any one of Embodiments 1-11, wherein the magnetic mesoporous nanoparticle has a pore size of approximately 7.5 nm to approximately 10.0 nm.

Embodiment 13 provides the magnetic mesoporous nanoparticle of any one of Embodiments 1-12, wherein the iron oxide is $Fe_3O_4$.

Embodiment 14 provides the magnetic mesoporous nanoparticle of any one of Embodiments 1-13, wherein the iron oxide is $Fe_2O_3$.

Embodiment 15 provides the magnetic mesoporous nanoparticle of any one of Embodiments 1-14, wherein one or more of the attributes of the magnetic mesoporous nanoparticle selected from particle size, pore size, surface area, number of pores, spacing of the pores, and added chemical functionality is chosen to encourage adsorption of a specific type of microorganism to the magnetic mesoporous nanoparticle.

Embodiment 16 provides a method of using magnetic mesoporous nanoparticles to sequester a microorganism from a media, including: contacting a mixture including one or more microorganisms and a media with one or more mesoporous nanoparticles, the nanoparticle including a mesoporous silicate nanoparticle and $Fe_3O_4$, thereby adsorbing the microorganisms to the pores or surface of the magnetic mesoporous nanoparticles; and exposing the magnetic mesoporous nanoparticles to a magnetic field, sufficient to concentrate the adsorbed microorganisms.

Embodiment 17 provides the method of Embodiment 16, wherein the microorganism includes algae.

Embodiment 18 provides the method of Embodiment 17, wherein the algae includes microalgae.

Embodiment 19 provides the method of any one of Embodiments 17-18, wherein the algae includes *Botryococcus, Chlamydomas, Chlorella, Crypthecodinium, Cyclotella, Cylindrotheca, Dunaliella, Haematococcus, Isochrysis, Monallanthus, Monoraphidium, Nannochloris, Nannochloropsis, Neochloris, Nitzschia, Phaeodactylum, Schizochytrium, Spirulina, Stichococcus, Synechocystis, Tagetes,* or *Tetraselmis*.

Embodiment 20 provides the method of any one of Embodiments 16-19, wherein the contacting causes flocculation of the microorganisms, the magnetic mesoporous nanoparticles, or a combination thereof.

Embodiment 21 provides the method of any one of Embodiments 16-20, where one type of microorganism is selectively adsorbed over another type of microorganism.

Embodiment 22 provides the method of any one of Embodiments 16-21, wherein the media includes water.

Embodiment 23 provides the method of any one of Embodiments 16-22, wherein the exposing to the magnetic field is sufficient to move the magnetic mesoporous nanoparticles towards the magnetic field.

Embodiment 24 provides the method of any one of Embodiments 16-23, wherein the exposure to the magnetic field is sufficient to gather a plurality of the magnetic mesoporous nanoparticles to an area.

Embodiment 25 provides the method of any one of Embodiments 16-24, wherein the exposure to the magnetic field is sufficient to cause flocculation of the magnetic mesoporous nanoparticles Embodiment 26 provides the method of any one of Embodiments 16-25, wherein the magnetic field is generated by an electromagnet.

Embodiment 27 provides the method of any one of Embodiments 16-26, further including separating the magnetic mesoporous nanoparticles with the adsorbed microorganisms from the media.

Embodiment 28 provides the method of Embodiment 27, wherein the separation includes transferring the media away from the adsorbed microorganisms.

Embodiment 29 provides the method of Embodiment 28, wherein the media is transferred using decanting, draining, centrifuging, siphoning, pumping, gravity, or a combination thereof.

Embodiment 30 provides the method of any one of Embodiments 27-28, wherein the separation removes at least approximately 60% to approximately 80% of the microorganisms from the media.

Embodiment 31 provides the method of any one of Embodiments 16-30, further including desorbing the adsorbed microorganisms from the magnetic mesoporous nanoparticles with the adsorbed microorganisms.

Embodiment 32 provides the method of Embodiment 31, wherein desorption includes washing, addition of chemical, heating, cooling, agitation, sonication, lysing, or addition or removal of solvent.

Embodiment 33 provides the method of any one of Embodiments 31-32, further including separating the desorbed microorganisms from the magnetic mesoporous nanoparticles.

Embodiment 34 provides the method of Embodiment 33, wherein separating the desorbed microorganisms from the magnetic mesoporous nanoparticles includes lysing, washing, sifting, air pressure treatments, or treatment with solvents.

Embodiment 35 provides the method of any one of Embodiments 16-34, wherein the microorganism is not killed.

Embodiment 36 provides the method of any one of Embodiments 27-35, wherein at least approximately 95% of the microorganisms adsorbed and separated survive.

Embodiment 37 provides the method of any one of Embodiments 27-36, wherein at least approximately 80% of the microorganisms adsorbed and separated survive.

Embodiment 38 provides the method of any one of Embodiments 27-37, wherein at least approximately 50% of the microorganisms adsorbed and separated survive.

Embodiment 39 provides the method of any one of Embodiments 33-38, further including reusing the separated magnetic mesoporous nanoparticles to adsorb microorganisms to the pores or surface of the nanoparticles.

Embodiment 40 provides the method of Embodiment 39, wherein the magnetic mesoporous nanoparticles are reused for at least 5 adsorption cycles.

Embodiment 41 provides the method of any one of Embodiments 39-40, wherein the magnetic mesoporous nanoparticles are reused for at least 10 adsorption cycles.

Embodiment 42 provides the method of any one of Embodiments 34-41, further including using the separated water for culturing microorganisms.

Embodiment 43 provides the method of any one of Embodiments 34-42, further including using the separated water for drinking water.

Embodiment 44 provides a method of making magnetic mesoporous nanoparticles, including: condensing an alkoxysilane, to give a mesoporous silicate nanoparticle; contacting the mesoporous silicate nanoparticle with an iron precursor, to give a magnetic mesoporous nanoparticle.

Embodiment 45 provides the method of Embodiment 44, further including co-condensing the alkoxysilane with a poly $((C_1-C_5)$alkyleneoxide) polyol.

Embodiment 46 provides the method of any one of Embodiments 44-45, further including after contacting the mesoporous silicate nanoparticle with the iron precursor, oxidizing or reducing the resulting product to give the magnetic mesoporous nanoparticle.

Embodiment 47 provides the method of any one of Embodiments 44-46, further including functionalizing the magnetic mesoporous nanoparticle with one or more amino $(C_1-C_{20})$alkyl groups with alkyl units covalently bound to the nanoparticle, wherein the $C_1-C_{20}$ alkyl groups are independently optionally interrupted by one or two —NH— groups.

Embodiment 48 provides a method of using magnetic mesoporous nanoparticles to sequester algae from water, including: contacting a mixture including algae and water with a plurality of magnetic mesoporous nanoparticles wherein the nanoparticle includes a mesoporous silicate nanoparticle and $Fe_3O_4$, thereby adsorbing the algae to the pores or surface of the magnetic mesoporous nanoparticles; exposing the magnetic mesoporous nanoparticles with the adsorbed algae to a magnetic field, sufficient to concentrate the adsorbed algae.

Embodiment 49 provides the method of Embodiment 48, further including: separating the magnetic mesoporous nanoparticles with the adsorbed algae from the water; desorbing the adsorbed algae from the magnetic mesoporous nanoparticles; separating the desorbed algae from the magnetic mesoporous particles; and reusing the magnetic mesoporous particles for another adsorption cycle.

Embodiment 50 provides the apparatus or method of any one or any combination of Embodiments 1-49 optionally configured such that all elements or options recited are available to use or select from.

What is claimed is:

1. A magnetic mesoporous nanoparticle, comprising:
a mesoporous silicate nanoparticle;
iron oxide; and
one or more amino$(C_1-C_{20})$alkyl groups with alkyl units covalently bound to the mesoporous silicate nanoparticle, wherein the $C_1-C_{20}$ alkyl groups are independently optionally interrupted by one or two —NH— groups;
wherein the magnetic mesoporous nanoparticle is magnetic and comprises a mesoporous structure.

2. The magnetic mesoporous nanoparticle of claim 1, further comprising at least one microorganism, wherein the microorganism is adsorbed to the pores or surface of the magnetic mesoporous nanoparticle.

3. The magnetic mesoporous nanoparticle of claim 2, wherein the microorganism is an algae.

4. The magnetic mesoporous nanoparticle of claim 3, wherein the algae comprises *Botryococcus, Chlamydomas, Chlorella, Crypthecodinium, Cyclotella, Cylindrotheca, Dunaliella, Haematococcus, Isochrysis, Monallanthus, Monoraphidium, Nannochloris, Nannochloropsis, Neochloris, Nitzschia, Phaeodactylum, Schizochytrium, Spirulina, Stichococcus, Synechocystis, Tagetes*, or *Tetraselmis*.

5. The magnetic mesoporous nanoparticle of claim 1, wherein the magnetic mesoporous nanoparticle has a particle size of approximately 150 nm to approximately 1200 nm.

6. The magnetic mesoporous nanoparticle of claim 1, wherein the magnetic mesoporous nanoparticle has a surface area of approximately 100 m$^2$/g to approximately 1000 m$^2$/g.

7. The magnetic mesoporous nanoparticle of claim 1, wherein the magnetic mesoporous nanoparticle has a pore size of approximately 5 nm to approximately 15 nm.

8. The magnetic mesoporous nanoparticle of claim 1, wherein the iron oxide is $Fe_3O_4$.

9. The magnetic mesoporous nanoparticle of claim 1, wherein the iron oxide is $Fe_2O_3$.

10. A method of using magnetic mesoporous nanoparticles to sequester a microorganism from a media, comprising:
contacting a mixture comprising one or more microorganisms and a media with one or more magnetic mesoporous nanoparticles each comprising a mesoporous silicate nanoparticle, $Fe_3O_4$, and one or more amino$(C_1-C_{20})$alkyl groups with alkyl units covalently bound to the mesoporous silicate nanoparticle, wherein the $C_1-C_{20}$ alkyl groups are independently optionally interrupted by one or two —NH— groups, thereby adsorbing the microorganisms to the pores or surface of the magnetic mesoporous nanoparticles; and
exposing the magnetic mesoporous nanoparticles to a magnetic field, sufficient to concentrate the adsorbed microorganisms.

11. The method of claim 10, wherein the contacting causes flocculation of the microorganisms, the magnetic mesoporous nanoparticles, or a combination thereof.

12. The method of claim 10, where one type of microorganism is selectively adsorbed over another type of microorganism.

13. The method of claim 10, wherein the magnetic mesoporous nanoparticle has a particle size of approximately 300 nm to about 600 nm.

14. The method of claim 10, further comprising separating the magnetic mesoporous nanoparticles with the adsorbed microorganisms from the media.

15. The method of claim 14, wherein at least approximately 50% of the microorganisms adsorbed and separated survive.

16. The method of claim 10, further comprising desorbing the adsorbed microorganisms from the magnetic mesoporous nanoparticles with the adsorbed microorganisms.

17. The method of claim 16, further comprising separating the desorbed microorganisms from the magnetic mesoporous nanoparticles.

18. The method of claim 17, further comprising reusing the separated magnetic mesoporous nanoparticles to adsorb microorganisms to the pores or surface of the nanoparticles.

19. The method of claim 10, wherein the microorganism is an algae.

* * * * *

UNITED STATES PATENT AND TRADEMARK OFFICE
CERTIFICATE OF CORRECTION

PATENT NO. : 8,828,705 B1  
APPLICATION NO. : 13/300343  
DATED : September 9, 2014  
INVENTOR(S) : Lin et al.

Page 1 of 1

It is certified that error appears in the above-identified patent and that said Letters Patent is hereby corrected as shown below:

On the title page, in column 2, under "Other Publications", line 12, delete "Nadorods" and insert --Nanorods--, therefor On the title page, in column 2, under "Other Publications", line 31, delete "Fe2O3" and insert --$Fe_2O_3$--, therefor On the title page, in column 2, under "Other Publications", line 38, delete "Fe3O4" and insert --$Fe_3O_4$--, therefor On page 2, in column 1, under "Other Publications", line 28, delete "brauniifor" and insert --braunii for--, therefor On page 2, in column 2, under "Other Publications", line 38, delete "brauniiKutz" and insert --braunii Kutz--, therefor In the specification, In column 2, line 32, delete "meganetic" and insert --magnetic--, therefor In column 5, line 63, delete "Algea" and insert --Algae--, therefor In column 6, line 13, delete "13" and insert --β--, therefor In column 8, line 27, after "example.", insert --¶--, therefor In column 14, line 42, delete "sauna" and insert --salina--, therefor Signed and Sealed this  
Twenty-second Day of March, 2016

Michelle K. Lee  
*Director of the United States Patent and Trademark Office*